US007871825B2

(12) United States Patent
Schwind

(10) Patent No.: US 7,871,825 B2
(45) Date of Patent: Jan. 18, 2011

(54) TEST ELEMENT AND METHOD FOR TESTING BLOOD

(75) Inventor: Peter Schwind, Fribourg (CH)

(73) Assignee: Medión Diagnostics AG, Dudigen (CH)

( * ) Notice: Subject to any disclaimer, the term of this patent is extended or adjusted under 35 U.S.C. 154(b) by 935 days.

(21) Appl. No.: 10/588,053

(22) PCT Filed: Feb. 2, 2005

(86) PCT No.: PCT/EP2005/001027

§ 371 (c)(1), (2), (4) Date: Dec. 29, 2006

(87) PCT Pub. No.: WO2005/072876

PCT Pub. Date: Aug. 11, 2005

(65) Prior Publication Data

US 2007/0218557 A1 Sep. 20, 2007

(30) Foreign Application Priority Data

Feb. 2, 2004 (DE) ....................... 10 2004 005 139

(51) Int. Cl.
*G01N 33/48* (2006.01)
*A61B 19/00* (2006.01)

(52) U.S. Cl. ......................... 436/63; 436/164; 436/165; 436/169; 436/174; 422/55; 422/56; 422/58; 422/99; 422/102; 604/7; 604/403; 604/404; 604/408

(58) Field of Classification Search ................... 436/63, 436/164, 165, 169, 174; 422/55, 56, 58, 422/61, 99, 102, 103; 604/7, 403, 404, 408
See application file for complete search history.

(56) References Cited

U.S. PATENT DOCUMENTS 3,502,437 A 3/1970 Mass
3,905,772 A 9/1975 Hartnett et al.
3,990,850 A 11/1976 Friedman et al.
4,055,394 A 10/1977 Friedman et al.
4,164,320 A 8/1979 Irazoqui et al.
4,650,662 A 3/1987 Goldfinger et al.
4,851,210 A * 7/1989 Hewett ...................... 435/7.25
4,900,321 A 2/1990 Kaufman et al.
4,906,439 A 3/1990 Grenner
5,287,264 A 2/1994 Arita et al.
5,429,119 A 7/1995 Griffin et al.
5,911,209 A 6/1999 Kouda et al.

(Continued)

FOREIGN PATENT DOCUMENTS

CA 2337899 2/2000

(Continued)

OTHER PUBLICATIONS

Translation of German Patent and Trademark Office Office Action for Application No. 10 2004005 139.9-53, dated Nov. 26, 2005.

*Primary Examiner*—Maureen M Wallenhorst
(74) *Attorney, Agent, or Firm*—RatnerPrestia

(57) ABSTRACT

A test for diagnostic tests, particularly for testing blood prior to a transfusion is disclosed. The test element includes at least two test units for carrying out at least two tests. The test element is provided with a fixing means for fixing the test element.

14 Claims, 2 Drawing Sheets

U.S. PATENT DOCUMENTS

| | | | |
|---|---|---|---|
| 6,372,182 | B1 | 4/2002 | Mauro et al. |
| 2002/0045805 | A1 | 4/2002 | Gopinathan et al. |
| 2004/0077934 | A1 | 4/2004 | Massad |

FOREIGN PATENT DOCUMENTS

| | | | |
|---|---|---|---|
| DE | 1005759 | | 9/1957 |
| DE | 43 13 253 | A1 | 10/1994 |
| DE | 196 40 904 | A1 | 4/1998 |
| DE | 202 15 268 | U1 | 4/2003 |
| EP | 51748 | A1 | 5/1982 |
| EP | 0 104 881 | | 4/1984 |
| EP | 638364 | B1 | 2/1995 |
| EP | 741296 | A1 | 6/1996 |
| EP | 0 741 296 | A1 | 11/1996 |
| EP | 0 779 103 | B1 | 6/1997 |
| JP | 59-75153 | | 4/1984 |
| JP | 64-500369 | | 2/1989 |
| JP | 10325839 | A | 12/1998 |
| RU | 2 088 921 | C1 | 8/1997 |
| RU | 2 147 123 | C1 | 3/2000 |
| RU | 2 191 382 | C2 | 10/2002 |
| WO | WO 87/07304 | | 12/1987 |
| WO | WO 01/73426 | A2 | 10/2001 |

* cited by examiner

TEST ELEMENT AND METHOD FOR TESTING BLOOD

CROSS-REFERENCE TO RELATED APPLICATIONS

This application is a U.S. National Phase Application of PCT International Application PCT/EP2005/01027, filed Feb. 2, 2005, incorporated herein by reference, which claims priority on German Patent Application DE 10 2004 005 139.9, filed Feb. 2, 2004.

FIELD OF THE INVENTION

The invention relates to a test element and a method for diagnostic tests, in particular for testing of bag and recipient blood before a blood transfusion.

BACKGROUND OF THE INVENTION

One of the greatest risks regarding transfusions of blood constituents, so-called blood transfusions, is a blood-group incompatibility between bag and recipient blood. The reasons for this are more often mix-ups than false determinations. For these reasons, so-called ABO identity tests are compulsory in some countries, which are carried out by the treating personnel, e.g. the nurse or the transfusing doctor, immediately before the transfusion at the patient's bed. These tests lead to additional stress of the station personnel which have little training in lab diagnostics and are amongst others rejected for this reason in some countries.

In certain countries as for example Germany or Austria, such an identity test is compulsory, however, only with regard to the recipient blood. In these countries, it is left to the respective hospital whether it carries out the identity test of the bag at the patient's bed or not. This is justified with the responsibility of the producer (blood bank) for the correct determination and designation of the bag blood. However, this does not prevent many hospitals from checking the bag blood type in the hospital lab once more and/or to carry out an ABO identity test at the patient's bed.

SUMMARY OF THE INVENTION

The object of the present invention is to practically eliminate the risk of mixing up during a blood transfusion without increasing the effort. Moreover, the costs for the blood transfusion shall not increase thereby.

In accordance with the invention, this object is solved by a test element for diagnostic tests and a method for testing during the preparation and performance of blood transfusions, as it is described in the independent claims. The inventive test element for diagnostic tests, in particular for testing blood before a blood transfusion comprises at least two test units for carrying out at least two tests. Further, the test element comprises a fixing means for fixing the test element. Preferably, the fixing element is formed in such a way that a test element may be fixed to a blood bag.

By means of such a test element, the danger of mixing up a blood bag and thus the application of blood with non-compatible blood type during a blood transfusion may practically be excluded. Preferably, by means of one of the at least two test units of the test element, the bag blood is tested for the blood transfusion, in other words the blood of a segment of the blood bag. Thereby, the test element is formed in such a way that the result of the test may be read off after a short period of time without any additional aids.

By means of the inventive fixing element, the complete test element may be fixed at the respective blood bag. Thereby, everybody can see that at this blood bag a confirming blood-type test has been carried out and which result this blood-type test provides. Further, by using the inventive test element, the confirming test may be carried out with few manual steps and in a short period of time. Additionally, the inventive test element comprises the advantage that further mistakes, as e.g. scribal errors, may practically be excluded.

In a preferred embodiment of the invention, bonding foil or cable binders are used as fixing elements.

The second inventive test unit of the test element is preferably used to further reduce the danger of application of a blood bag with unsuitable blood type. To this end, the blood of the recipient of the blood transfusion is preferably tested immediately before the transfusion by means of the second test unit of the test element. The aids being necessary therefore, namely the test element, are physically connected with the blood bag and is thus inevitably provided at the patient's bed.

Preferably, the two test units of the test element are arranged in such a way that, after performing both tests, it is easy to recognize whether the blood type of the blood bag matches with the blood type of the recipient or not. This is achieved preferably by a laterally reversed arrangement of the test chambers—for fluid indicator reagents—or the test fields—for immobilized indicator reagents—of the test units.

In a further preferred embodiment the test unit for the bag blood comprises at least three test chambers or test fields, in which respectively an anti-A, an anti-B, and an anti-D reagent is contained. By means of these at least three test chambers respectively test fields, an ABD test may accordingly be carried out. In a further preferred embodiment, a further test chamber respectively a further test field for carrying out self-control is provided. The test unit for the blood of the recipient comprises preferably at least two test chambers respectively two test fields, in which preferably an anti-A and an anti-B reagent is contained. By means of these at least two test chambers respectively test fields, an ABO test may be carried out.

If fluid indicator reagents shall be used, in a further preferred embodiment at least one of the test units for carrying out the tests is formed in such a way that the test chamber for receiving the indicator reagent is closed or closable and after the performance of the test, no fluid emerges therefrom, i.e. by evaporation, so that in the case of reactions in the fluid phase, the test unit does not dry out and thereby the test carried out at the patient may be compared with the test carried out at the blood bag later on. To this end, for example suitable closing mechanisms may be applied.

In a further preferred embodiment the test unit for the bag blood comprises at least three test chambers or test fields, in which respectively an anti-A, an anti-B, and an anti-D reagent is contained. By means of these at least three test chambers respectively test fields, an ABD test may accordingly be carried out. In a further preferred embodiment, a further test chamber respectively a further test field for carrying out self-control is provided. The test unit for the blood of the receptor comprises preferably at least two test chambers respectively two test fields, in which preferably an anti-A and an anti-B reagent is contained. By means of these at least two test chambers respectively test fields, an ABO test may be carried out.

According to the invention, this object is solved also by a method for testing blood during the preparation and performance of blood transfusions, wherein the method comprises the steps of:

testing the bag blood by means of the first test unit in a test element, as described above, preferably in the hospital lab, fixing the test element at the blood bag containing the bag blood by means of a fixing means, and testing the blood of the recipient by means of a second test unit of the test element, preferably at the patient's bed, in particular within 45 days after testing the bag blood.

The inventive method for testing blood comprises the advantage that an application of a blood bag with a blood type being incompatible for the patient may practically be excluded during blood transfusion. By the application of a test element, which may be fixed to the blood bag for testing the bag blood and the blood of the recipient, a mix-up is practically impossible, since it is clearly visible which tests have already been carried out for the blood transfusion, in which the blood bag shall be applied and what the result of the respective tests was. The nurse who is rather untrained in diagnostic tests is provided with a reference result through the real result of the lab test being visible for her in situ, which facilitates for her the evaluation whether her own result is correct. This saves time-consuming inquiries at the hospital lab.

In addition, the nurse is substantially disburdened by blood bag testing in the lab. Further, the inventive method enables that the blood bags are clearly marked and thus no records have to be checked.

Preferably, this method is used for testing blood types. Further preferred it is verified before the performance of the blood transfusion that during testing of the bag blood and during testing of the recipient blood the same blood type has been identified.

BRIEF DESCRIPTION OF THE DRAWINGS

In the following, an exemplary embodiment of the invention is illustrated by means of the attached drawings, in which.

DETAILED DESCRIPTION OF THE INVENTION

Figure 1:
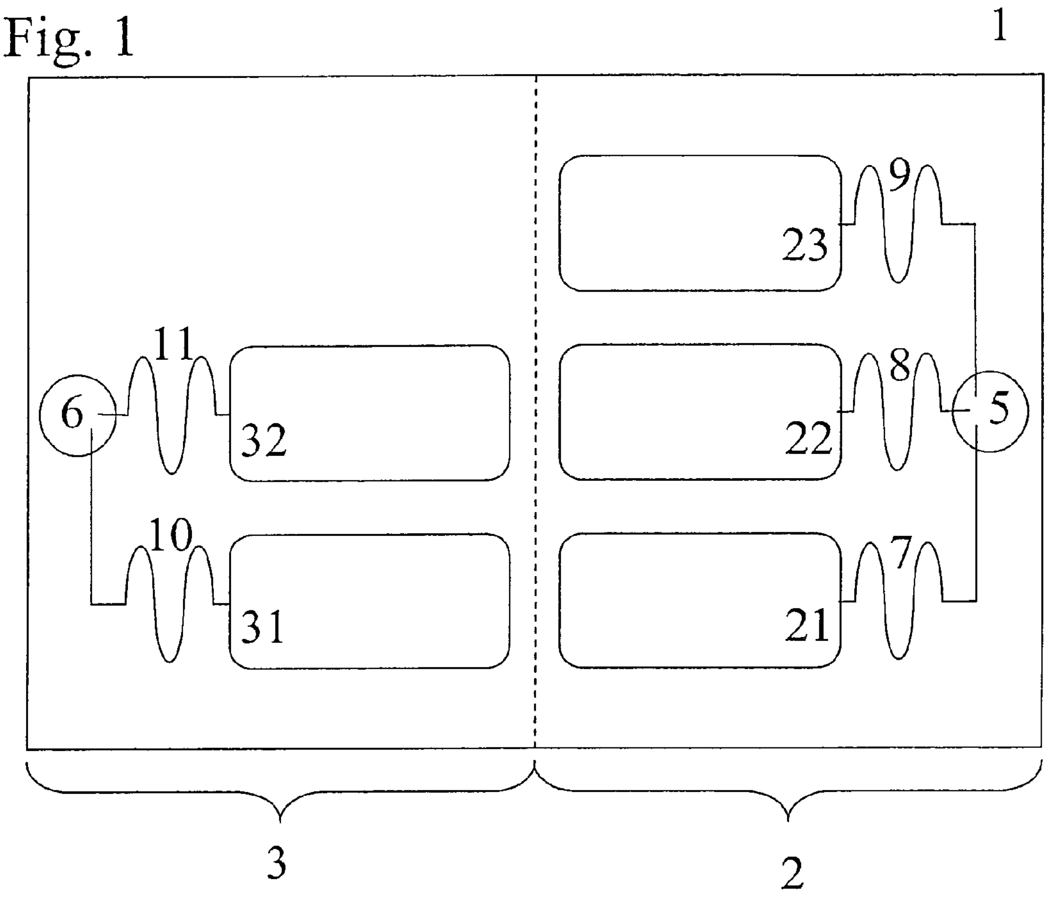
FIG. 1 shows a plan view of a preferred embodiment of an inventive test element.

FIG. 1 shows a test element 1 with a test unit 2 for testing the bag blood and a test unit 3 for testing the receptor blood. An example for such a test element is described in the international patent application PCT/EP03/10590 [WO/2004/028692] of the applicant.

Each test unit 2, 3 comprises its own inlet 5, 6 for the fluid to be tested. In the illustrated example, LUER LOK® inlets are considered to which e.g. syringes may be connected.

In the test unit 2 for the bag blood, three channels 7, 8, 9 begin at the inlet 5, through which the fluid to be tested, preferably blood, flows to the reaction chambers 21, 22, 23. In the embodiment illustrated in FIG. 1, the first chamber 21 comprises an anti-A reagent, the second chamber 22 an anti-B reagent, and the third chamber 23 an anti-D reagent. By means of this test unit, the information on the blood bag is verified.

In the embodiment shown in FIG. 1, the second test unit 3 comprises for the testing of the blood of the receptor two channels 10, 11, through which the fluid to be tested flows from the inlet 6 to the reaction chambers 31, 32. In order to carry out an ABO test with this test unit 3, one reaction chamber 31 comprises an anti-A reagent and the other reaction chamber an anti-B reagent. In the present exemplary embodiment, the chambers of the two test units with the same contents are arranged laterally reversed, in order to facilitate a comparison of the two test results.

FIG. 1 provides reaction chambers for the application of fluid reagents.

Figure 2:
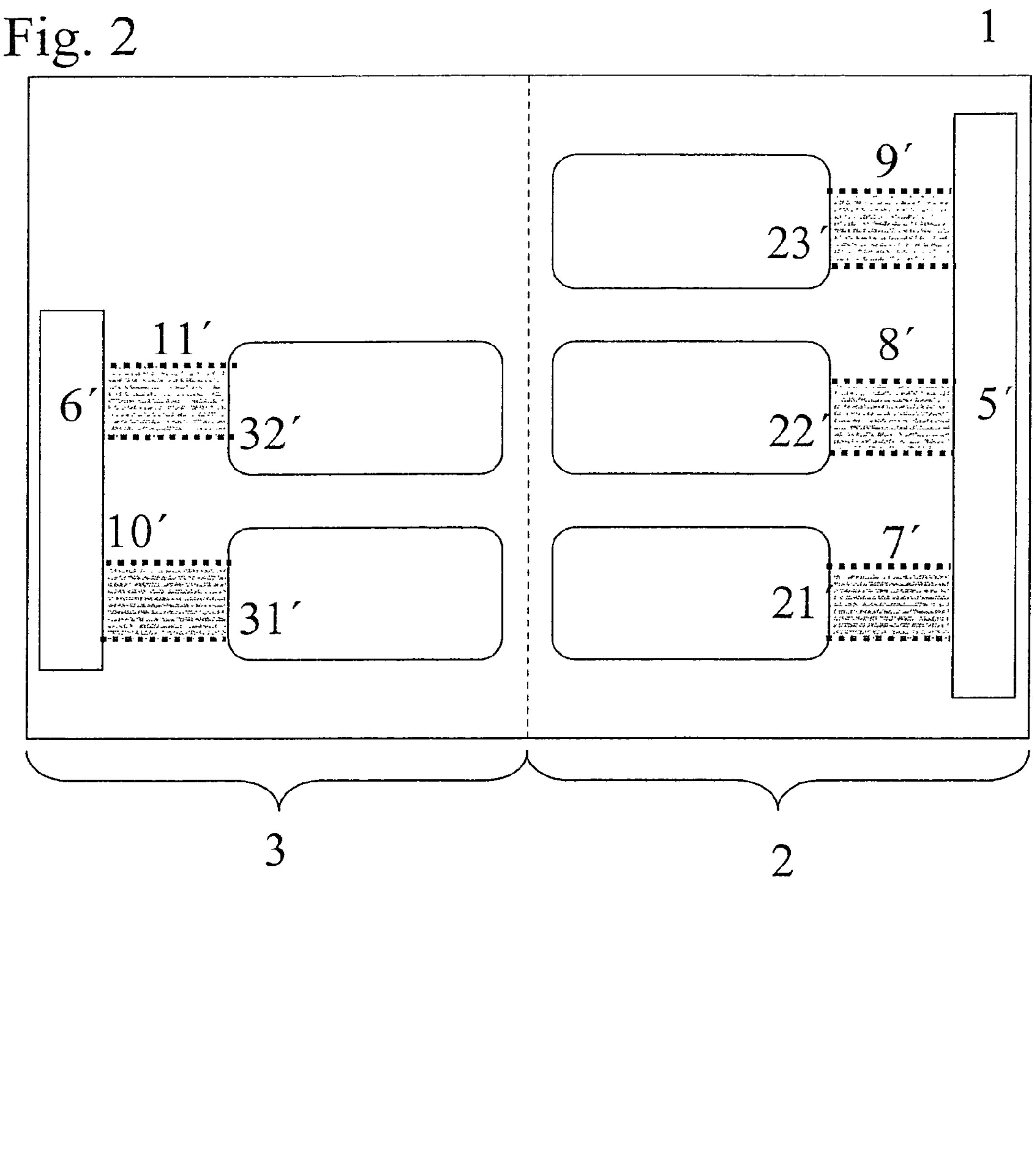
FIG. 2 shows a plan view of a further preferred embodiment of an inventive test element.

FIG. 2 shows another embodiment of the inventive test element, which is suitable for immobilized reagents. The test element 1 is also in this case divided into two test units 2, 3. The test units 2, 3 comprise two, respectively three test fields 21', 22', 23' respectively 31', 32' corresponding to the test chambers with the same reference signs without apostrophe in FIG. 1. In these test fields, the indicator reagents being necessary for the test are immobilized in a suitable way, i.e. bound. The blood is applied to the test fields 21', 22', 23' respectively 31', 32' via surfaces 5', respectively 6' for applying the blood and via supplying surfaces 7', 8', 9' respectively 10', 11'—for example porous separation membranes for example of nitro cellulose in which blood is movable, corresponding to the channels with respective reference signs without apostrophe in FIG. 1. The test element illustrated here is formed in such a way that the supplying surfaces 7', 8', 9' respectively 10', 11' are arranged in one plane beneath the surface of the test element 1. When the blood reaches the test fields 21', 22', 23' respectively 31', 32' which are separated from the surface of the test element 1 by a layer being at least transparent in the area of a window, a reaction occurs with the indicator reagents. This reaction may be monitored through the transparent area of the covering of the test fields. Examples for such a test unit are contained in the unpublished German application with the application number 103 30 982.9 dated Jul. 9, 2003.

Figure 3:
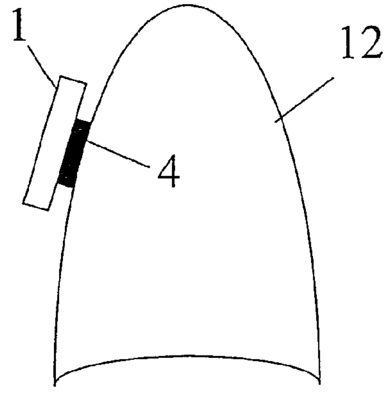
FIG. 3 shows an example for the fixation of the test element at a blood bag.

FIG. 3 shows a test element 1 which has been fixed to a blood bag 12 by means of fixing means 4, wherein the fixing means is preferably pre-associated with the test means.

Preferably, the fixing means 4 consists of a bonding strip on the backside of the test element 1. This bonding strip may be self-bonding and may be covered before the application with a releasable covering band.

The fixing means 4 may also consist of an engagement equipment, which may engage in a corresponding counterpart on a blood bag 12, in such a way that it is no longer removable or only by means of a tool—for example a key.

The invention claimed is:

1. A method for testing blood during the preparation and performance of bedside-tests, wherein the method comprises:

first, testing donor blood located within a blood bag to be potentially transfused into a recipient by using a first test unit of a test element and obtaining a first result;

subsequently, fixing the test element to the blood bag;

thereafter, testing blood from the recipient by applying a sample of the recipient's blood to a second test unit of the test element while the test element is fixed to the blood bag and obtaining a second result; and comparing the first and second test results on the test element fixed to the blood bag in order to determine whether the donor blood is compatible for transfusion into the recipient.

2. A test element for carrying out the method according to claim 1, wherein the test element comprises at least a first test unit and a second test unit for performing at least two tests, and the test element comprises a fixing means for fixing the test element to the blood bag.

3. The test element according to claim 2 in which the fixing means is a bonding foil.

4. The test element according to claim 2 in which the fixing means is provided as a cable tie.

5. The test element according to claim 2 in which at least one of the first and second test units is formed in such a way that, after the performance of the tests, no fluid emerges.

6. The test element according to claim 2 in which by means of one of the at least first and second test units, bag blood for blood transfusions is tested.

7. The test element according to claim 6, wherein the first test unit for bag blood comprises at least three test chambers or test fields.

8. The test element according to claim 7, wherein three of the at least three test chambers or test fields respectively comprise anti-A, anti-B, and anti-D reagents.

9. The test element according to claim 2 in which by means of the second test unit, the blood of a recipient of a blood transfusion is tested.

10. The test element according to claim 9, wherein the second test unit for the blood of a recipient comprises at least two test chambers or test fields.

11. The test element according to claim 10, wherein two of the at least two test chambers or test fields respectively contain anti-A and anti-B reagents.

12. The test element according to claim 2, wherein in at least one of the first and second test units, a test result is maintained for at least 45 days.

13. The method according to claim 1, wherein the testing of blood from the blood bag occurs in the hospital laboratory.

14. The method according to claim 1, wherein the testing of blood from the recipient occurs at the bed of the recipient.

* * * * *